United States Patent

Loison et al.

[11] Patent Number: 5,902,735
[45] Date of Patent: *May 11, 1999

[54] FUNCTIONAL DNA BLOCK AND PLASMID CODING FOR HIRUDIN, TRANSFORMED YEAST, METHOD FOR HIRUDIN, HIRUDIN OBTAINED, AND ITS PHARMACEUTICAL USE

[75] Inventors: Gérard Loison, Strasbourg; Yves Lemoine, Strasboug-Neudorf; Nathalie Labat, Strasbourg; Alain Balland, Truchtersheim, all of France

[73] Assignee: Noechst AG, Germany

[*] Notice: This patent is subject to a terminal disclaimer.

[21] Appl. No.: 08/708,543

[22] Filed: Sep. 5, 1996

Related U.S. Application Data

[63] Continuation of application No. 08/405,765, Mar. 11, 1995, Pat. No. 5,591,640, which is a continuation of application No. 08/264,241, Jun. 22, 1994, abandoned, which is a continuation of application No. 07/967,546, Oct. 27, 1992, abandoned, which is a continuation of application No. 07/623,256, Dec. 5, 1990, abandoned, which is a continuation of application No. 07/430,954, Nov. 1, 1989, abandoned, which is a continuation of application No. 07/072,173, Jul. 10, 1987, abandoned.

[30] Foreign Application Priority Data

Jul. 10, 1986 [FR] France ................................ 86 10090
Oct. 1, 1986 [FR] France ................................ 86 16722

[51] Int. Cl.⁶ .......................... C12P 21/06; C12N 15/00; C07H 17/00; C07K 14/815
[52] U.S. Cl. .................... 435/69.7; 435/69.7; 435/320.1; 435/325; 435/252.3; 536/23.4; 536/23.5; 530/300
[58] Field of Search .......................... 530/300; 536/23.1; 435/69.1, 69.7, 240.1, 320.1, 71.1, 69.2, 325

[56] References Cited

U.S. PATENT DOCUMENTS

5,591,640  1/1997  Loison et al. ...................... 435/320.1

OTHER PUBLICATIONS

Bergmann et al. 1968. Biol Chem Hoppes Seyler 367:731–740.
Dodt et al. 1984. FEBS Letters 165(2):180–184.

*Primary Examiner*—Karen Cochrane Carlson
*Attorney, Agent, or Firm*—Burns, Doane, Swecker & Mathis, L.L.P.

[57] ABSTRACT

The invention relates to a functional DNA block by means of which hirudin may be prepared from yeast, which block contains at least the sequence:

$-S_{tr}-L_{ex}-S_{cl}-H$ gene

H gene being the gene coding for hirudin or one of its variants, $S_{tr}$ is a DNA sequence containing the signals which provide for the transcription of the H gene by yeast, $L_{ex}$ is a leader sequence needed in order to obtain the excretion of the gene product, $S_{cl}$ is a DNA sequence coding for the site of cleavage by yscF proteinase, which cleavage site is unique and situated in the hirudin precursor immediately upstream from the H gene.

The invention relates more especially to a functional DNA block in which the H gene codes for HV1.

7 Claims, 10 Drawing Sheets

PSTI-BGLII DOUBLE DIGESTION
CLONING IN M13TG131 AT THE PSTI/BAMHI SITES

Hibridization of M13TG897 DNA with the oligon. for
the mutagenesis (a) 5'-TCTTTGGATAAAAGAATTACGTATACAGAC-3'
(b) 3'... ...TTCCCCATAGAAACCTATTTTCTTAATGCATATGTCTGACG... ... 5'

Elongation of the complementary strand
with Klenow polymerase

Ligation, E. coli transformation (c) 3'... ...TTCCCCATAGAAACCTATTTTCTTAATGCATATGTCTGACG... ... 5'

IN VITRO MUTAGENESIS

* Opening with BglII
* Generation of deletions by action of Bal31
* Insertion of a BamHI site 1 base pair upstream from the MFalpha1 initiator ATG

* Digestion of pTG892 DNA with <u>SalI</u> and <u>BamHI</u>.
* Isolation of the shortest DNA fragment.
* Cloning of the fragment between the SalI and BamHI sites of the polylinker of M13tg120.

M13tg889

STRUCTURE OF M13TG889

*Fig. 7*

```
                    YSCF endopeptidase cleavage
                                 ↓
pheromone α ··· Lys Arg Glu Ala Glu Ala Trp His ··· pTG886 ··· Lys Arg Glu Ala Glu Ala Trp Leu Gln Val Asp Gly Ser Met Ile Thr pTG897 ··· Lys Arg Glu Ala Glu Ala Ile Thr ··· pTG1805 ··· Lys Arg Glu Ala Glu Ala Lys Arg Ile Thr ··· pTG1818 ··· Lys Arg Glu Ala Glu Ala Ser Leu Asp Lys Arg Ile Thr ··· pTG1828|
          | ··· Lys Arg Ile Thr ···
   pTG1833|
```

*Fig. 8*

```
HIND III
         1                    ↓               4
AGCTTCTTTGGATAAAAGAGTCGTATACACTGACTGCACCGAATCCGGTCAGAA..
    AGAAACCTATTTTCTCAGCATATGTGACTGACGTGGCTTAGGCCAGTCTT..
         2          ↑         3         ↑    5

↓    6                    ↓              8
CCTGTGCCTGTGCGAAGGTTCTAACGTTTGCGGTCAGGGTAACAAA..
GGACACGGACACGCTTCCAAGATTGCAAACGCCAGTCCCATTGTTT..
         ↑    7                          ↑

↓    10              ↓    11
TGCATCCTCGGATCCGACGGTGAAAAAAACCAGTGCGTTACAGGTGAA..
ACGTAGGAGCCTAGGCTGCCACTTTTTTTGGTCACGCAATGTCCACTT..
         9    ↑                    12   ↑

↓    14                    ↓
GGTACTCCGAAACCGCAGTCTCATAACGACGGTGACTTCGAA..
CCATGAGGCTTTGGCGTCAGAGTATTGCTGCCACTGAAGCTT..
         13        ↑         15

17        ↓    19
GAAATTCCAGAAGAATCTTGCAGTAATAAGATCTG
CTTTAAGGTCTTCTTAGAACGTCATTATTCTAGACAGCT
    ↑    16             ↑    18        SALI
```

Fig. 9

```
                      1-HinfI                           2-HinfI
      1-AluI          1-AccI                            1-HpaII
    1 V              V    V                             V    V
      AGCTTCTTTGGATAAAAGAGTCGTATACACTGACTGCACCGAATCCGGTC
      1              18   23                           41   45

1-MaeIII
                    1-MaeII                          1-NsiI
                      V                       V      V    100
      AGAACCTGTGCCTGTGCGAAGGTTCTAACGTTTGCGGTCAGGGTAACAAA
                      78                     93      100

1-Sav3A
              2-BinI
              1-XhoII
              1-NlaIV
              1-BinI
              1-BamHI
          1-MnlI
          1-FokI                         2-MaeIII
          1-SfaNI      1-HphI             2-HphI 1-RsaI
    101   VV V    VV    V                 V      V    V
          TGCATCCTCGGATCCGACGGTGAAAAAAACCAGTGCGTTACAGGTGAAGGTACT
          102    110  119                137      143  150
            103  110
              106 110
                  110
                   111
                   111

1-XmnI
                                          1-MboII
                                         1-TaqI
                                         1-AsuII
                                      3-MaeIII
                                      3-HphI                2-MboII
                                       VV    VV  V          V    200
          CCGAAACCGCAGTCTCATAACGACGGTGACTTCGAAGAAATTCCAG
                                179   185                   200
                                   180  186
                                        188
                                         188
                        2-Sav3A
                        2-XhoII
                        1-BglII
    201                   VV                                         30
          AAGAATACTTGCAGTAATAAGATCTG-------------------I
                          220
                          220
                          221
```

Fig 10

```
11
ATG GTA GTT TAT ACC GAC TGC ACC GAA TCC
Met Val Val Tyr Thr Asp Cys Thr Glu Ser

41
GGT CAG AAC CTG TGC CTG TGC GAA GGT TCT
Gly Gln Asn Leu Cys Leu Cys Glu Gly Ser

71
AAC GTT TGC GGT CAG GGT AAC AAA TGC ATC
Asn Val Cys Gly Gln Gly Asn Lys Cys Ile

101
CTC GGA TCC GAC GGT GAA AAA AAC CAG TGC
Leu Gly Ser Asp Gly Glu Lys Asn Gln Cys

131
GTT ACA GGT GAA GGT ACT CCG AAA CCG CAG
Val Thr Gly Glu Gly Thr Pro Lys Pro Gln

161
TCT CAT AAC GAC GGT GAC TTC GAA GAA ATT
Ser His Asn Asp Gly Asp Phe Glu Glu Ile

191
CCA GAA GAA TAT TTA CAA TGA AAA ATG AAA
Pro Glu Glu Tyr Leu Gln xxx Lys Met Lys 221                                  251
GAA TAT CAA TCA TAG AGA ATT TTG ATT T
Glu Tyr Gln Ser xxx Arg Ile Leu Ile xxx
```

FUNCTIONAL DNA BLOCK AND PLASMID CODING FOR HIRUDIN, TRANSFORMED YEAST, METHOD FOR HIRUDIN, HIRUDIN OBTAINED, AND ITS PHARMACEUTICAL USE

This application is a continuation of application Ser. No. 08/405,765, filed Mar. 16, 1995, now U.S. Pat. No. 5,591,640 which is a continuation of Ser. No. 264,241, filed Jun. 22, 1994, now abandoned, which is a continuation of Ser. No. 07/967,546, filed Oct. 27, 1992, now abandoned, which is a continuation of Ser. No. 07/623,256, filed Dec. 5, 1990, now abandoned, which is a continuation of Ser. No. 07/430,954, filed Nov. 1, 1989, now abandoned, which is a continuation of Ser. No. 07/072,173, filed Jul. 10, 1987, now abandoned.

The present application relates to improvements made to French Patent Application No. 85/06,672. It relates to vectors for the expression of a protein having the activity or leech hirudin (H. medicinalis).

Patent Application No. 85/06,672 describes a method by means of which yeasts such as S. cerevisiae may be caused to produce hirudin, which is secreted into the culture medium in active form.

The present invention relates to new vectors which provide for the production of hirudin, in particular HV1, under improved conditions.

More especially, the present invention relates to functional DNA blocks by means of which hirudin may be prepared from yeasts, which blocks contain at least the sequence:

$$-S_{tr}-L_{ex}-S_{cl}-\text{H gene}$$

H gene being the gene coding for hirudin or one of its variants; the H gene is preferably, according to the present invention, the gene coding for HV1 or HV2; optionally, the H gene may be followed by a yeast terminator sequence, for example that of the PGK gene;

$S_{tr}$ is a DNA sequence containing the signals providing for the transcription of the H gene by yeast;

$L_{ex}$ is a leader sequence needed in order to obtain the gene product;

$S_{cl}$ is a DNA sequence coding for the site of cleavage by yscF proteinase, which cleavage site is unique and situated in the hirudin precursor immediately upstream from the H gene; furthermore, the element $S_{cl}$-H gene can be repeated several times.

This type of expression block enables a single, mature and correct protein to be obtained.

In effect, with the construction described in Patent Application No. 85/06,672, S. cerevisiae produces hirudin in the form of a precursor having two cleavage sites for yscF proteinase, a product of the KEX2 gene (1). The endopeptidase activity of yscF is necessary to the maturation of this hirudin precursor. However, only the cleavage events at the second site, that which is more remote from the $NH_2$ end of the precursor, permit the release of active hirudin; in contrast, when the cleavage takes place at the first site and not at the second, a longer form is secreted which differs from hirudin by an extension of amino acid residues at the $NH'_2$ end. This latter undesirable form can contaminate the mature and correct hirudin during different stages of purification, and can thereby complicate the purification process and give rise to a drop in yield in the preparation of pure hirudin.

In the present invention, yeast is caused to synthesize a hirudin precursor which possesses only a single cleavage site for yscF, so that its maturation to hirudin leads to the secretion of only the desired form.

Among $L_{ex}$ sequences, there should be mentioned, in particular, the so-called "prepro" sequence which permits the excretion of the alpha sex pheromone of yeast.

As an example of a secretion system, that of the alpha pheromone was chosen, that is to say, in the above sequence, $L_{ex}$ sequence originates from the gene for the alpha sex pheromone of yeast, but other systems could be used (for example the killer protein system) (4).

Preferably, it is advantageous that the yeasts which are hosts for the plasmids carrying the functional blocks according to the invention should be able to be of either mating type and should be able, in addition, to be cultured in the absence of a selection pressure.

Under these conditions, the transformed yeasts are especially convenient to use at the industrial level.

For this purpose, the present invention proposes DNA expression blocks as described above but in which the $S_{tr}$ sequence contains a promoter of a yeast gene other than the MFalpha1 gene promoter; this may be, for example, the PGK gene promoter of yeast.

In effect, in the constructions described in Patent Application No. 85/06,672, the gene for the hirudin precursor is transcribed from the MFalpha1 gene promoter. This promoter functions at its maximum power in strains of mating type Matalpha. The choice of host is hence restricted to this type of strain, which excludes strains of the mating type Mata as well as diploid or polyploid devoid of a mating type. In particular, this excludes the yeast strains used in industry which most frequently fall into this latter category. By changing the promoter, it is possible to obtain an expression of hirudin independent of the mating sign of the host strain.

In general, these DNA blocks will be carried by plasmids containing, in addition, an origin of replication in yeasts, for example the origin of replication of the $2\mu$ plasmid.

To facilitate the construction of the vectors, these plasmids may be "coli/yeast shuttles" and may contain elements which permit their replication in E. coli, for example an origin of replication such as that of pBR322 and a selection marker such as $amp^R$. These plasmids will also contain a selection marker for yeast, for example a gene coding for resistance to certain toxic chemical compounds or a gene enabling an auxotrophy to be complemented; more especially, the URA3 gene will be used.

In effect, it has been shown in patent WO 86/01,224 that the introduction of certain mutations which confer resistance to 5-FU in a ura3 strain transformed to ura+ by means of a plasmid permitted a larger choice of media for culturing these transformed strains. It was possible, in particular, to use the industrial complex media.

The present invention relates more especially to the synthesis and secretion of the variant HV1.

The HV1 gene has already been chemically synthesized for the purpose of expressing it in E. coli (French Patent No. 84/13,250).

Most of the synthetic oligonucleotides used in patent 84/13,250 have been retained for the construction of the sequence coding for the precursor of HV1, with the exception of those which permit the various junctions with sequences which will be fused upstream and downstream from the sequence.

The production of a secreted hirudin requires the presence of a precursor containing the information needed for the secretion and for the correct maturation of this polypeptide according to the normal metabolic pathway occurring in yeast. In Patent Application No. 85/06,672, it has been shown that the NH$_2$-terminal sequence of the precursor of the alpha factor could be used for the secretion of the variant HV2 of hirudin. The present invention relates to the application of this system to the secretion of the variant HV1.

The invention relates in particular to a functional DNA block by means of which hirudin may be prepared from yeast, which block contains at least:

the HV1 gene;

a DNA sequence ($S_{tr}$) containing the signals which provide for the transcription of the HV1 gene by yeast.

This function block, integrated in a plasmid or the chromosomes of a yeast, preferably of the genus Saccharomyces, may, after transformation of the said yeast, enable hirudin to be expressed, either in active form, or in the form of an inactive precursor capable of regenerating hirudin by activation.

These functional blocks preferably possess the following structure:

-$S_{tr}$-$L_{ex}$-$S_{cl}$-H gene-

H gene being the gene coding for HV1; the H gene is, where appropriate, followed by a yeast terminator sequence such as that of the PGK gene;

$S_{tr}$ is a DNA sequence containing the signals which provide for the transcription of the H gene by yeast;

$L_{ex}$ is a leader sequence needed in order to obtain the excretion of the gene product;

$S_{cl}$ is a DNA sequence coding for a cleavage site containing, where appropriate, at the 3' end, before the H gene, an ATG codon or two colons coding for Lys-Arg or five codons coding for Ser-Leu-Asp-Lys-Arg;

furthermore, the element $S_{cl}$-H gene can be repeated several times.

Among $L_{ex}$ sequences, there should be mentioned that for the alpha sex pheromone of yeast, and for $S_{tr}$, there should be mentioned the MFalpha1 gene promoter and also the PGK gene promoter, but other sequences can be used; in particular, as an example of a secretion system, that of the alpha pheromone was chosen, that is to say, in the above sequence, the $L_{ex}$ sequence originates from the gene for the alpha sex pheromone of yeast, but other systems could be used (for example the killer protein system) (4).

In order to direct the expression and secretion of hirudin into the culture medium, the corresponding gene is integrated in a vector for yeast or a plasmid which includes the functional block described above and at least one origin of replication in yeasts. The plasmid will preferably contain the following elements:

the origin of replication of the 2$\mu$ plasmid of yeast, the ura3 gene, an origin of replication in *E. coli* and a marker for resistance to an antibiotic, the 5' region of the MFalpha1 gene, which includes the transcription promoter, the leader sequence and the prepro sequence of the precursor of the alpha factor; this sequence will be fused, in phase, upstream from the coding sequence for hirudin HV1, the transcription terminator of the PGK gene of yeast, which will be placed downstream from the hirudin gene.

In general, the expression blocks according to the invention may be integrated in a yeast, especially, Saccharomyces, either in an autonomously replicating plasmid or in the chromosome of the yeast.

When the plasmid is autonomous, it will contain elements which provide for its replication, that is to say an origin of replication such as that of the 2$\mu$ plasmid. Furthermore, the plasmid may contain selection elements such as the URA3 or LEU2 gene, which provide for complementation of ura3$^-$ or leu2$^-$ yeasts. These plasmids can also contain elements which provide for their replication in bacteria when the plasmid has to be a "shuttle" plasmid, for example an origin of replication such as that of pBR322, a marker gene such as Amp$^r$ and/or other elements known to those versed in the art.

The present invention also relates to the yeasts transformed by an expression block according to the invention, which is either carried by a plasmid or integrated in its chromosomes, especially the strains of Saccharomyces and particularly the strains of *S. cerevisiae,* in particular those of mating type Mata or alternatively the diploid or polyploid strains devoid of a mating type, but above all the ura yeast strains transformed to ura$^+$ by a plasmid according to the invention and which have become resistant to 5-fluorouracil, these strains being capable of culture on industrial medium.

When the promoter is that of the gene for the alpha pheromone, the yeast will preferably be of mating type Matalpha. For example, a strain of genotype ura3$^-$ or Leu2$^-$ or the like will be used, complemented by the plasmid to provide for the maintenance of the plasmid in the yeast by a suitable selection pressure.

Finally, the present invention relates to a method for preparing hirudin or one of its variants, by fermentation of a yeast transformed as described above, on a culture medium, and recovery of the hirudin produced in the culture medium in mature form or in the form of a precursor of hirudin which is capable of maturation in vitro or in vivo, as well as the hirudin or its variants obtained by this method.

Thus, although it is possible to prepare hirudin by fermentation of the above transformed strains on an appropriate culture medium and by accumulation of hirudin in the cells, it is nevertheless preferable to cause the hirudin to be secreted into the medium, either in mature form or in the form of a precursor which will have to be processed in vitro.

This maturation can be carried out in several stages. In the first place, it may be necessary to cleave certain elements originating from the translation of the $L_{ex}$ sequence; this cleavage will be performed on the sequence corresponding to $S_{cl}$. The mature hirudin may be preceded by a methionine which will be selectively cut with cyanogen bromide. This method is useable because the coding sequence for hirudin does not include methionine.

It is also possible to envisage at the N-terminal end the dipeptide Lys-Arg, which is cut to COOH by a specific endopeptidase; since this enzyme is active in the secretion process, the mature protein may, in consequence, thereby be obtained directly in the medium. However, in some cases, it may be necessary to provide for an enzymatic cleavage after secretion by adding a specific enzyme.

In some cases, especially after the treatment with cyanogen bromide, it may be necessary to renature the protein by re-creating the disulfide bridges. For this purpose, the peptide is denatured, for example with guanidinium chloride, and then renatured in the presence of reduced glutathione and oxidized.

Finally, the invention relates to the hirudin obtained by the methods according to the invention.

The hirudin thereby obtained may be used by way of a thrombin inhibitor, as an anticoagulant drug, as a laboratory product for preventing coagulation and/or as a diagnostic agent using the labeled product.

In particular, HV1 can be used in pharmaceutical compositions, alone or in combination with other active principles, or alternatively in the context of tests or diagnosis, in vitro or in vivo. In the latter case, it can be advantageous to label the molecule, for example with a radioactive, fluorescent, enzyme or other label.

The examples which follow will illustrate other characteristics and advantages of the present invention.

Figure 3:
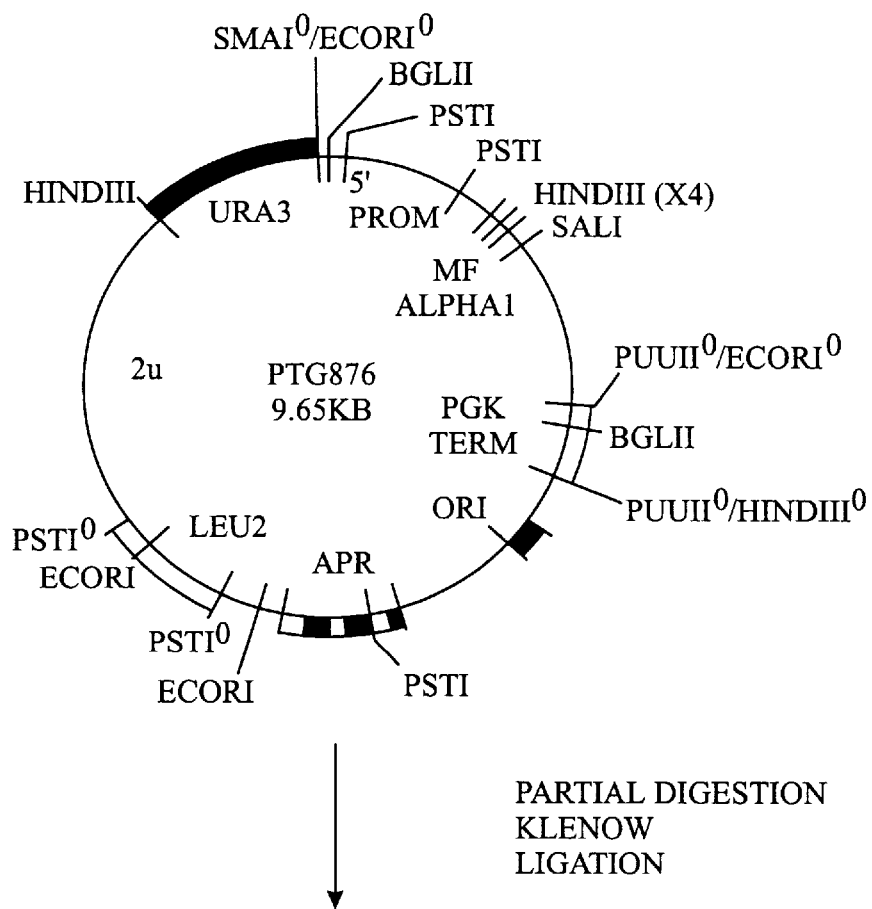
Figure 3:
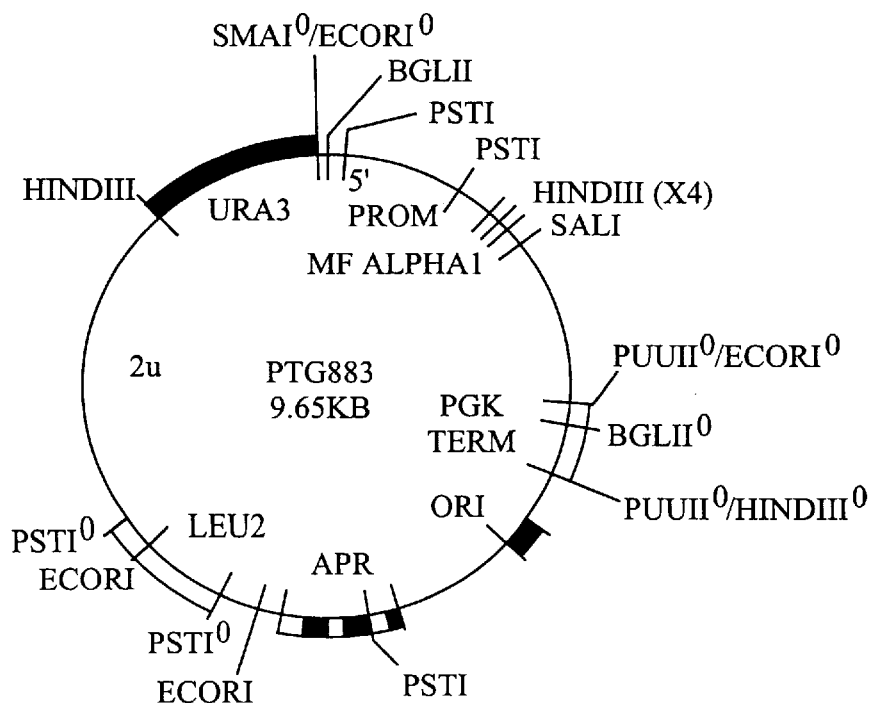
Figure 4:
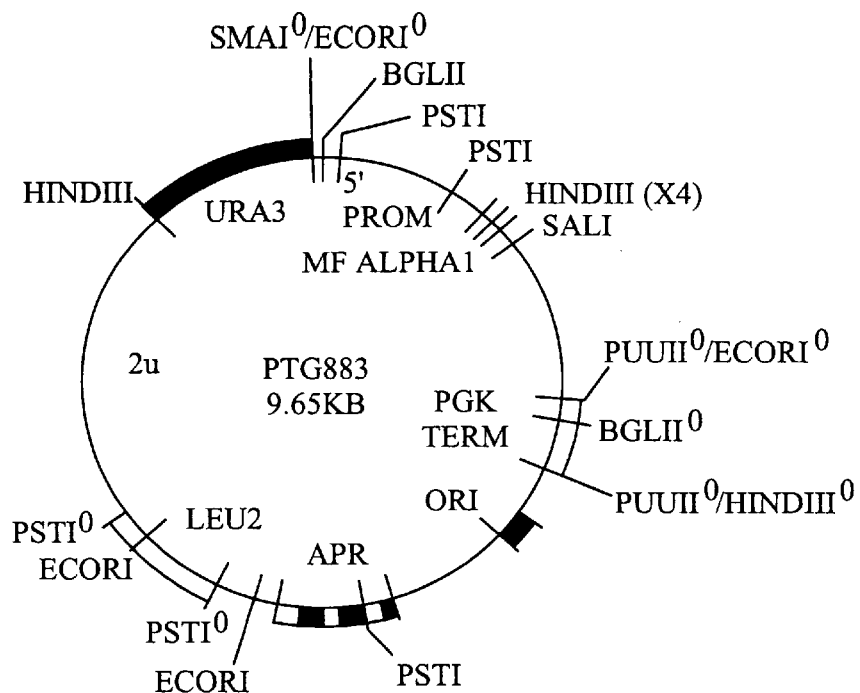
Figure 4:
Figure 4:
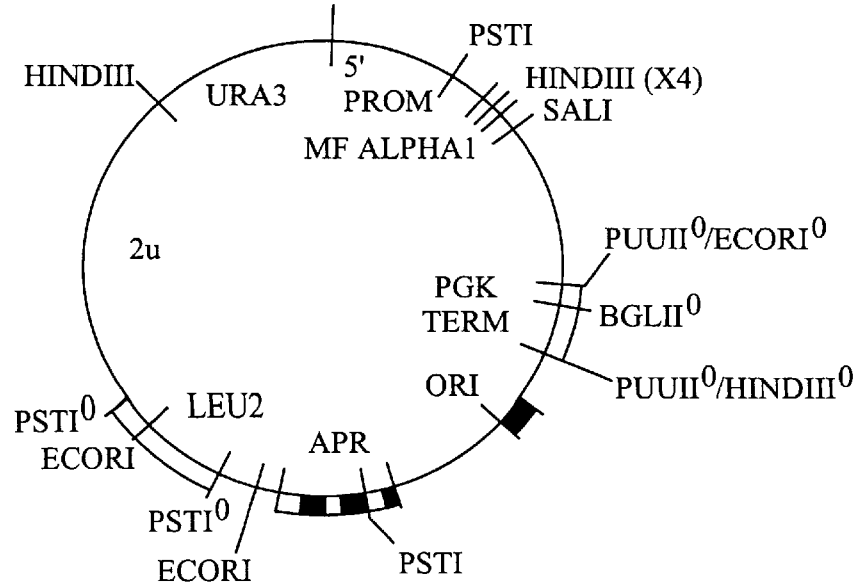
Figure 5:
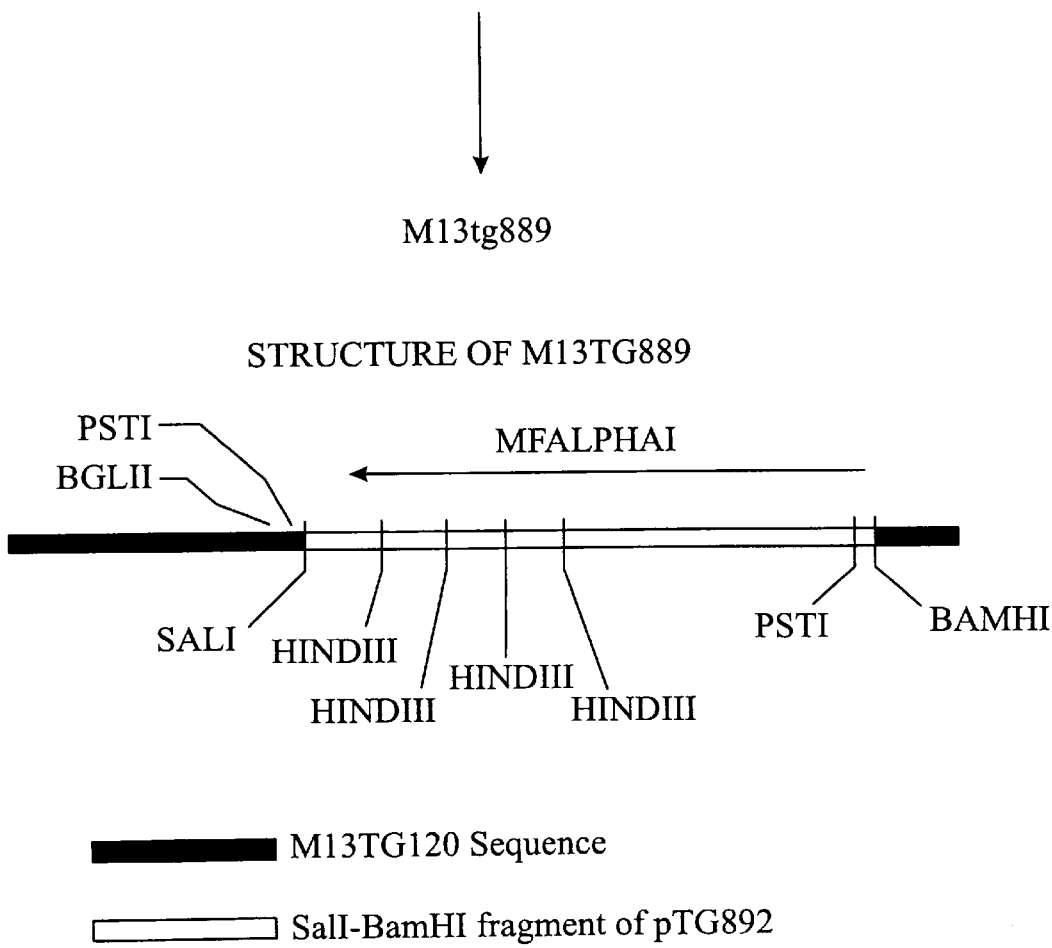
Figure 6:
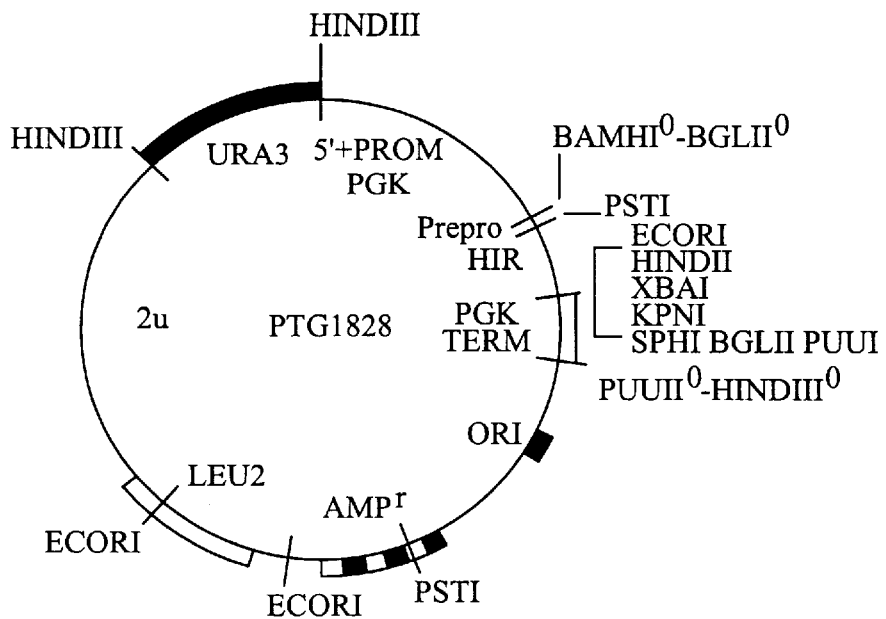
Figure 6:
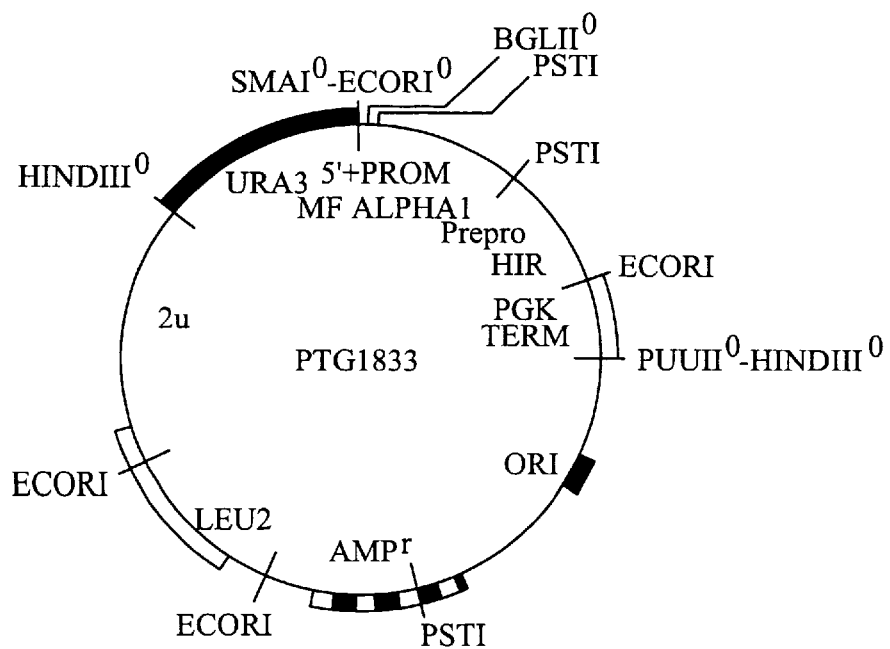

a) sequence of the oligonucleotide for the mutagenesis, b) partial sequence of the M13TG897 DNA hybridizing with the oligonucleotide, c) mutated sequence, FIG. 3 shows the construction of pTG883, FIG. 4 shows the construction of pTG892, FIG. 5 shows the construction of M13TG889, FIG. 6 shows the structure of pTG1828 and pTG1833, FIG. 7 shows the structure of the hirudin precursor corresponding to the sequences carried by different plasmids; the junction between a) the cleavage site (Lys Arg) closest to the $NH_2$ end of the precursor and b) the mature sequence of hirudin HV2 ($NH_2$-Ile-Thr etc.) have been shown.

FIG. 8 shows the sequences and the position of the oligonucleotides used for the synthesis of the DNA sequence coding for HV1, FIGS. 9 and 10 show the restriction map, and the translation of the sequence to amino acids, relating to the synthesis of the DNA sequence coding for HV1.

The plasmids and strategies used and described in Patent Application No. 85/06,672 are not repeated in the present application.

EXAMPLE 1

Plasmid pTG897 carries the information for a hirudin precursor which contains only a single cleavage site for yscF proteinase. Maturation at this cleavage site releases an inactive hirudin. Cleavage with yscF proteinase releases a hirudin molecule elongated at the $NH_2$-end by 4 residues Glu Ala Glu Ala. The deletion of the DNA fragment coding for this Glu Ala Glu Ala sequence would enable a correctly processed hirudin chain to be released. This deletion was carried out by the technique of directed in vitro mutagenesis.

Figure 1:
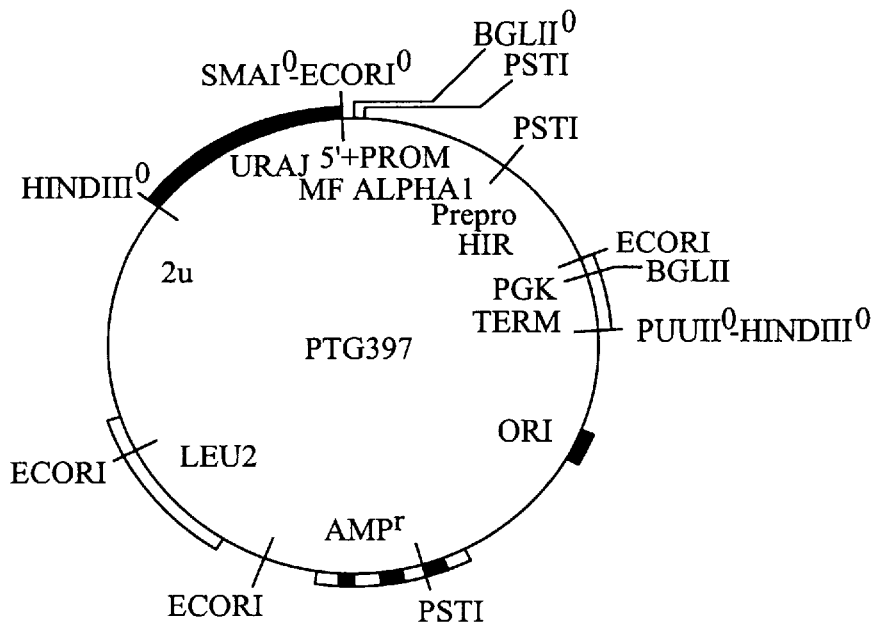
FIG. 1 shows the construction and structure of M13TG897.
Figure 1:
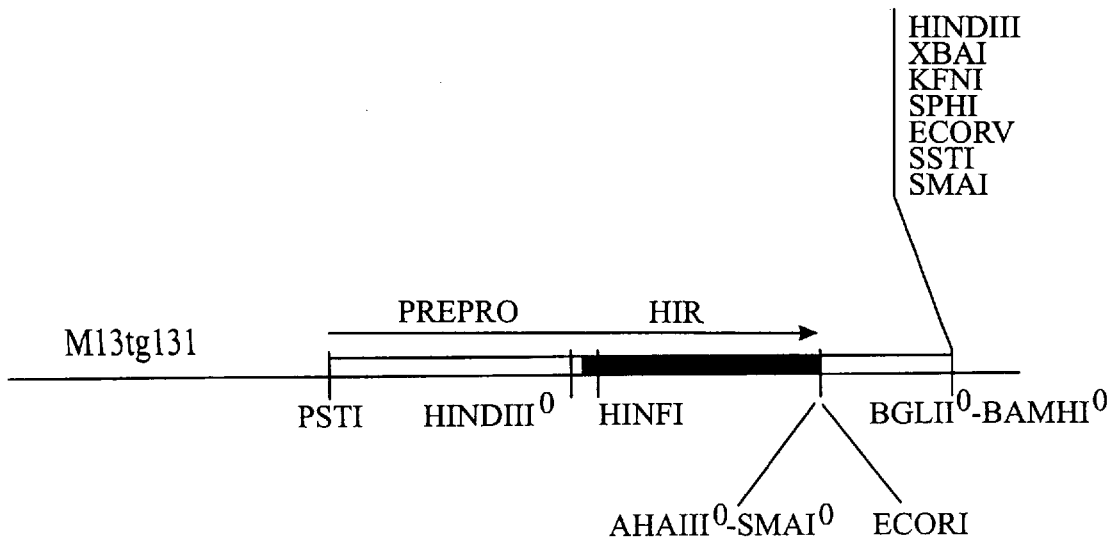

Plasmid pTG897 was cut up by PstI/ BglII double digestion; the DNA fragments including the hirudin sequence was cloned into the replicative form of the single-stranded phage M13TG131 to give the phage M13TG897 (FIG. 1).

Figure 2:
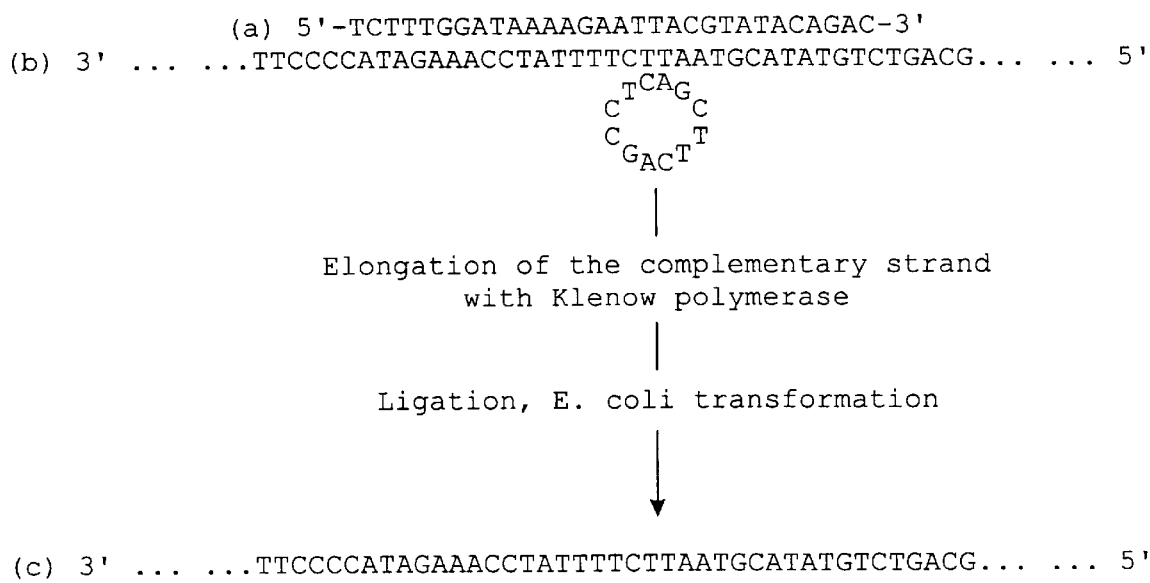
FIG. 2 shows the in vitro mutagenesis of the phage DNA of M13TG897 to M13TG1827.

An oligonucleotide having the sequence:

5'-TCTTTGGATAAAAGAATTACGTATACAGAC-3'
was hybridized with the genomic DNA of this phage M13TG897. The first half of this oligonucleotide (15 base pairs) hybridizes with the 15-base pair sequence directly upstream from the sequence to be deleted, and its second half hybridizes with the 15-base pair sequence directly downstream (FIG. 2). This oligonucleotide served as a template for the in vitro synthesis of the complementary strand of the phage M13TG897 genome. After the action of T4 DNA ligase, designed to seal covalently the newly formed strand, a receptor bacterium (for example JM103 [Δ(Lac-Pro) SupE Thi End1A sbcB15 strA rk– mk+/F' TraD36 ProAB+ LacIQ LacZ Δ M15], is transfected and the phages derived from this transfection are analysed by DNA-DNA hybridization using as a probe the oligonucleotide described above and labeled with $^{32}p$ by kinase treatment, according to the customary techniques practiced by those versed in the art (2). This correctly mutated phage DNA forms, with the oligonucleotide for the mutagenesis, a hybridization complex which is identifiable by its greater stability and its greater resistance to stringent conditions, whereas the hybridization complex formed by the unmutated phage DNA and the oligonucleotide is destabilized by the presence of a single-stranded DNA loop.

EXAMPLE 2

Transfer of the mutated fragment into a new expression vector

Plasmid pTG883 is derived from plasmid pTG876 by simply eliminating the 8glII site present close to the transcription terminator of the PGK gene.

For this purpose, this plasmid pTG876 was partially digested with BglII, the Klenow fragment of *E. coli* DNA polymerase I was then reacted in the presence of the 4 nucleotides and the DNA molecules were linked covalently to one another by means of the action of phage T4 DNA ligase. Plasmid pTG883 now possesses only a single BglII site, situated upstream from the promoter of the pheromone gene (FIG. 3).

Plasmid pTG883 (20 μg) was linearized by BglII digestion and then subjected to a controlled digestion with Ba131 nuclease (1.4 units, 10 minutes—Boehringer Mannheim) according to the customary techniques. The DNA treated in this manner was purified by successive extractions with phenol and chloroform/isoamyl alcohol, and a fraction (5 μg) was then subjected to the action of Klenow polymerase in order to obtain a maximum of blunt ends. The DNA treated in this manner was ligated with non-phosphorylated BamHI linkers (5'-CGGATCCCG) in the presence of phage T4 ligase, according to the technique described by lathe et al (3). After transformation of *E. coli* 1106 and selection for resistance to ampicillin, a plasmid pTG892 was isolated which was deleted in respect of the 5' region flanking the MFalpha1 gene (FIG. 4), the BamHI linker being localized one base upstream from the ATG according to the scheme:

5'- CGGGATCCCG A ATG AGA TTT . . .

BamHI linker MTalpha$_{1-2}$ coding portion

The new BamHI-SalI fragment thereby obtained was cloned between the BamHI-SalI sites of the phage M13TG120 to give the phage M13TG889 (FIG. 4). The BamHI-BglII fragment containing all the coding portion for the alpha pheromone was isolated from the phage M13TG889 and ligated with the large BglII fragment of plasmid pTG848. The plasmid obtained after ligation, pTG892b, contains the BamHI-BglII fragment corresponding to the coding portion for the pheromone which is inserted behind the BglII side of the PGK gene promoter.

The pTG892b DNA includes a single BglII site and a single SalI site; the two sites enclose a short sequence which includes a PstI. By double digestion with BglII and SalI, elution of the large fragment and ligation with a synthetic polylinker, the short sequence was replaced by the synthetic polylinker. This polylinker, having the sequence:

5'- G AT C C A G C T G A C AT C T G C AT G C G
    GTCGACTGTAGACGTACGCAGCT-5' has one end which is cohesive with the fragments liberated by BglII and one end which is cohesive with fragments liberated by SalI, as well as recognition sites for, inter alia, the enzymes PvuI, BglII and SphI.

The new vector thereby obtained was referred to as pTG1819. The DNA of this vector was digested with the enzymes SphI and PstI. By means of this double digestion, three fragments are obtained: a 6.5-kb PstI-PstI, a 1.9-kb PstI-SphI and another 0.5-kb SphI-PstI fragment.

The two longer fragments were purified and mixed with the SphI-PstI fragment corresponding to the mutated hirudin and originating from the phage M13TG1827; a new expression vector, pTG1828, was thereby obtained (FIG. 6).

EXAMPLE 3

Transfer of the fragment into the vector pTG881: new plasmid pTG1833 pTG881 DNA was partially digested with PstI so as to liberate a 6.1-kb fragment. This fragment was isolated and then completely digested with BglII, thereby liberating 2 PstI-PstI and PstI-BglII fragments. These two fragments were ligated with the 0.62-kb PstI-BglII fragment derived from pTG1828. A new vector, pTG1833, which differs from plasmid pTG897 only by the deletion of the sequences coding for Glu Ala Glu Ala, is thereby reconstituted. The structure of the precursor thereby formed is shown in FIG. 7. This plasmid pTG1833 possesses an origin of replication for E. coli, a gene for resistance to ampicillin, the Leu2 gene of S. cerevisiae, a fragment of the 2µ plasmid which permits replication in S. cerevisiae, the MFalpha$_1$ gene promoter coding for prepro and the hirudin gene (FIG. 6).

EXAMPLE 4

Transformation of yeast with plasmids pTG1828 and pTG1833

S. cerevisiae strain TGY1sp4 (Matalpha ura3-251-373-328 his3-11-15) was transformed with plasmids pTG1818, pTG1828 and pTG1833. The results recorded in Table 1 show that pTG1818 and pTG1833 induce the secretion of the same level of hirudin activity. In contrast, TGY1sp4 pTG1828 secretes half as much hirudin activity as the other two strains. A strain TGY1sp4 pTG881 which does not possess the genetic information for hirudin was included as a control. The production of hirudin secreted by S. cerevisiae (Mat a) strains TGY14-1, transformed either with pTG1828 or with pTG1833, and TGY14-2, transformed with the same plasmids, was also compared (Table 2). In this instance also, it is noted that, in the case of the strain TGY14-2 (mating type Matalpha), plasmid pTG1833 induces better secretion of hirudin than plasmid pTG1828. In contrast, in the case of the strain TGY14-1 (mating type Mat a), pTG1833 does not induce hirudin secretion, as expected, whereas TGY14-2 produces hirudin.

TABLE 1

Antithrombin activity of the yeast culture supernatants (10 ml) (48 h of culture, YNBG medium and 0.5% casamino acids)

| Receptor | Plasmid | Total activity |
| --- | --- | --- |
| TGY1sp4 | pTG881 | not detectable |
|  | pTG1818 | 158 |
|  | pTG1828 | 73 |
|  | pTG1833 | 149 |

TABLE 2

Antithrombin activity of the yeast culture supernatants (10 ml) (72 h of culture, YNBG medium + 0.5% casamino acids)

| Receptor | Plasmid | Total activity |
| --- | --- | --- |
| TGY14-1 | pTG881 | not detectable |
|  | pTG1828 | 54 |
|  | pTG1833 | not detectable |
| TGY14-2 | pTG881 | not detectable |
|  | pTG1828 | 103 |
|  | pTG1833 | 210 |

EXAMPLE 5

Isolation of strains capable of being cultured in complete medium without loss of the plasmid phenotype It has been shown in patent WO 86/01,224 that the introduction of certain mutations conferring resistance to 5-FU in a ura3 strain transformed to ura+ by means of a plasmid permitted a larger choice of media for culturing these transformed strains; In particular, the industrial complex media could be used. From the strain TGY1sp4 pTG1833, spontaneous mutants were isolated which were capable of forming colonies on complete medium (YPG) supplemented with 1 mg/ml 5-fluorouracil according to the protocol described in patent WO 86/01,224. 6 mutants were cultured in complete medium, and one of these was chosen which produced no colony from which the effects of the plasmid were absent after more than 20 generations of growth under non-selective conditions.

The mutant, referred to as TGY1sp4-3, can be used for the production of hirudin in complete medium.

EXAMPLE 6

Strategy for the synthesis of the DNA sequence coding for HV1

This sequence will have to carry the elements which permit fusion of the HV1 sequence in phase with the prepro portion of MFalpha1, and the signals which permit correct maturation of the secreted hirudin; in particular, the junction region will contain a Lys-Arg pair immediately upstream from the first NH$_2$-terminal residue of HV1.

The strategy employed is similar to that described in French Patent No. 84/13,250. The synthesis is carried out in two separate blocks which are then assembled as a result of their BamHI cohesive ends. The first block comprises 9 oligonucleotides numbered from 1 to 9 and the second block comprises 10 nucleotides numbered from 10 to 19. Their sequences and the position of the oligonucleotides are shown in FIG. 8.

The restriction map and also the translation of the sequence to amino acids are given in FIGS. 9 and 10.

EXAMPLE 7

Assembly of the synthetic gene

First synthetic block

The oligonucleotides 2 to 8 (FIG. 8) were phosphorylated at their 5' ends to avoid the formation of dimers or polymers: 500 picomoles of each oligonucleotide were treated with polynucleotide kinase (2 units) in a final volume of 25 µl of 60 mM Tris-HCl, pH 7.5, 10 mM MgCl$_2$ and 8 mM dithiothreitol, containing 3.3 pmol of [$^{32}$P]-gamma-ATP (5,000 Ci/nmol); after 15 minutes' incubation at 37° C., 5 nmol of unlabeled ATP are added.

After incubation at 37° C. for 30 minutes, the complementary fragments were hybridized in pairs, with the exception of the fragments 1, 2 and 3, these latter being mixed together. 300 pmol of each oligonucleotide were used in a final 10 μl volume of 66 mM Tris HCl, pH7.5, 6 mM MgCl$_2$, 100 mM NaCl, 0.5 mM spermidine and 8 mM DTT.

These mixtures, heated to 100° C. for 3 minutes, are then cooled slowly to 37° C. during 2 hours. The hybridized oligonucleotides 1–2–3 were mixed with the oligonucleotides 4–5 and incubated at 37° C. for 2 hours. In the same manner, the hybridization was performed of the pairs of oligonucleotides 6–7 with 8–9. In a final stage, the 9 oligonucleotides pretreated in this manner were brought together and incubated for 2 hours at 37° C. in a final volume of 100 μl.

14 pmol of these hybridized oligonucleotides were subjected to treatment with T4 ligase for 15 hours at 15° C. 50 ng of the large HindIII-BamHI fragment of M13TG131, purified beforehand on gel, were then added to the reaction mixture. The ligation mixture was then used for transforming competent E. coli JM103 cells. Among 12 phage clones thereby obtained, only one possessed the desired sequence: M13TG1888.

Second synthetic block

The same strategy was used for synthesizing the second block (FIG. 8), which was cloned between BamHI and SalI sites of the phage of M13TG131. Two of the 12 clones tested possessed an insert corresponding to the desired sequence. One of these clones was designated M13TG1889.

Assembly of the synthetic gene

The two double-stranded DNAs of M13TG1888 and M13TG1889 were digested with HindIII and BamH1 and with BamHI and SalI, respectively, and mixed with the large HindIII-SalI fragment of pBR322 which had been purified on gel. After ligation, the mixture was used to transform E. coli 1106. By selection for resistance to ampicillin, plasmid pTG1890, which contains the correctly reconstituted synthetic sequence, was obtained.

EXAMPLE 8

Construction of the vector pTG1891 which enables the synthesized hirudin to be secreted The DNA fragment of pTG1890 which carries the coding sequence for HV1 is taken up in the form of a HindIII-BglII fragment (BglII site being situated immediately upstream from the SalI site which was used for the above cloning) and inserted between the HindIII and BglII sites of plasmid pTG881 described in Patent Application No. 85/06,672. In the resulting plasmid, pTG1891, the HV1 gene is hence present inserted between the prepro sequences of MFalpha1 and the transcription terminator; this construction must hence provide for the maturation and secretion of hirudin HV1, since it is identical to pTG1818 (Patent No. 85/06,672) with the exception of the coding sequences for HV2, which are replaced by those for HV1.

EXAMPLE 9

Transformation of a strain TGY1sp4 with plasmid pTG1891 DNA

The strain TGY1sp4 (alpha-1 ura3-251-373-328, His3-11-15) was transformed with plasmid pTG1891; 2 clones obtained by selection for the ura$^+$ character were cultured and their production of hirudin, secreted into the culture medium, was determined. As a control, the amount of hirudin secreted by TGY1sp4 pTG1818 was assayed under the same conditions.

Twice as much antithrombin activity was measured in the culture supernatant of the strain TGY1sp4 pTG1891 (0.9 mg/l of culture supernatant) than in that of the strain TGY1sp4 pTG1833.

Deposition of strains representing the invention

The following strains were deposited at the Collection Nationale de Cultures de Microorganismes (National Collection of Microorganism Cultures) of the Institut Pasteur, 28 rue du Docteur Roux, 75724 Paris Cedex 15:

* on Jun. 6, 1986:
    Saccharomyces cerevisiae TGY1sp4 pTG1828, under no. I-569
    Saccharomyces cerevisiae TGY1sp4.3pTG1833, under no. I-570
* on Nov. 6, 1986:
    Saccharomyces cerevisiae TGY1sp4 pTG1891, under no. I-623

REFERENCES

1) Achstetter, T. and Wolf, D. H. (1985) EMBO Journal 4, 173.
2) Zoller, M. J. and Smith M. H. (1983) Meths in Enzym. 100, 469.
3) Lathe, R., Kieny, M. P., Skory, S. and Lecocq J-P (1984)DNA 3, 173.
4) Bussey H., Saville D., Greene D. et al. (1983) Mol. Cell. Biol. 3, 1362–1370.

We claim:

1. An expression cassette for producing a hirudin variant protein from yeast which comprises:

a first DNA fragment encoding a precursor of a hirudin variant protein, said precursor comprising a hirudin variant and an an additional region having more than 2 amino acids and linked by a peptide bond to the N-terminal end of said hirudin variant, wherein said additional region comprises a single cleavage site which is the dipeptide Lys-Arg recognized by the yscF proteinase, which constitutes the C-terminal end of said additional region;

a second DNA fragment encoding a leader sequence wherein said second DNA fragment is directly linked in the same reading frame with the 5' end of said first DNA fragment, and wherein the leader sequence is the "pre-pro" precursor of the α-factor; and a third DNA fragment comprising an origin of replication functional in yeast and a promoter of a yeast gene other than the MFalpha 1 gene promoter wherein said third DNA fragment is linked to said first and second DNA fragments such that said first and second DNA fragments are expressed.

2. A plasmid which comprises the expression cassette according to claim 1.

3. a yeast cell comprising the expression cassette according to claim 1 wherein said cassette is functionally integrated into said yeast cell.

4. A process for producing a hirudin variant which comprises the steps of:

culturing the yeast cell according to claim 3 under conditions such that said hirudin variant is produced; and isolating said hirudin variant thus produced.

5. A plasmid which comprises an expression cassette for producing a hirudin variant protein from yeast, wherein said expression cassette comprises:

a first DNA fragment encoding a precursor of a hirudin variant protein, said precursor comprising a hirudin variant and an an additional region having more than 2 amino acids and linked by a peptide bond to the N-terminal end of said hirudin variant, wherein said additional region comprises a single cleavage site which is the dipeptide Lys-Arg recognized by the yscF proteinase, which constitutes the C-terminal end of said additional region;

a second DNA fragment encoding a leader sequence wherein said second DNA fragment is directly linked in the same reading frame with the 5' end of said first DNA fragment; and a third DNA fragment comprising an origin of replication functional in yeast and a promoter of a yeast gene other than the MFalpha 1 gene promoter wherein said third DNA fragment is linked to said first and second DNA fragments such that said first and second DNA fragments are expressed.

6. A yeast cell comprising an expression cassette for producing a hirudin variant protein from yeast, wherein said expression cassette comprises:

a first DNA fragment encoding a precursor of a hirudin variant protein, said precursor comprising a hirudin variant and an an additional region having more than 2 amino acids and linked by a peptide bond to the N-terminal end of said hirudin variant, wherein said additional region comprises a single cleavage site which is the dipeptide Lys-Arg recognized by the yscF proteinase, which constitutes the C-terminal end of said additional region;

a second DNA fragment encoding a leader sequence wherein said second DNA fragment is directly linked in the same reading frame with the 5' end of said first DNA fragment; and a third DNA fragment comprising an origin of replication functional in yeast and a promoter of a yeast gene other than the MFalpha 1 gene promoter wherein said third DNA fragment is linked to said first and second DNA fragments such that said first and second DNA fragments are expressed;

wherein said cassette is functionally integrated into said yeast cell.

7. A process for producing a hirudin variant which comprises the steps of:

culturing the yeast cell according to claim 6 under conditions such that said hirudin variant is produced; and isolating said hirudin variant thus produced.

* * * * *